(12) United States Patent
Brandt et al.

(10) Patent No.: US 6,649,072 B2
(45) Date of Patent: Nov. 18, 2003

(54) METHOD FOR PRODUCING AUTOLOGOUS PLATELET-RICH PLASMA

(76) Inventors: Robert Brandt, 16520 S. Tamiami Trail, Suite 18, Ft. Myers, FL (US) 33908; Michael Buzenius, 3515 Othello Dr., Naperville, IL (US) 60564

( * ) Notice: Subject to any disclaimer, the term of this patent is extended or adjusted under 35 U.S.C. 154(b) by 0 days.

(21) Appl. No.: 09/994,908

(22) Filed: Nov. 16, 2001

(65) Prior Publication Data

US 2003/0094425 A1 May 22, 2003

(51) Int. Cl.$^7$ .................. A61K 35/16; B01D 17/038
(52) U.S. Cl. .................. 210/782; 210/787; 210/789; 210/745; 424/529; 424/530; 424/531; 424/532; 435/366; 494/37
(58) Field of Search .................. 210/782, 781, 210/787, 745, 789; 424/529, 530, 531, 532; 435/366; 494/37

(56) References Cited

U.S. PATENT DOCUMENTS

| | | |
|---|---|---|
| 5,165,938 A | 11/1992 | Knighton |
| 5,211,850 A | 5/1993 | Shettigar et al. |
| 5,423,738 A | 6/1995 | Robinson et al. |
| 5,733,545 A | 3/1998 | Hood, III |
| 5,858,238 A | 1/1999 | McRea et al. |
| 6,010,627 A | 1/2000 | Hood, III |
| 6,214,338 B1 | 4/2001 | Antanavich et al. |
| 6,303,112 B1 | 10/2001 | Worden |
| 6,444,228 B1 * | 9/2002 | Baugh et al. ............ 424/530 |
| 2002/0054901 A1 * | 5/2002 | Gainey et al. ............ 435/366 |
| 2002/0147098 A1 * | 10/2002 | Dolecek ............ 494/37 |

FOREIGN PATENT DOCUMENTS

| | | |
|---|---|---|
| EP | 0 105 014 | 4/1984 |
| EP | 0 128 849 | 12/1984 |
| EP | 0 190 018 | 1/1985 |
| FR | 2 472 385 | 7/1981 |
| FR | 2 533 438 | 3/1984 |
| GB | 2 146 335 | 4/1985 |
| WO | WO 87/01728 | 3/1987 |

OTHER PUBLICATIONS

Knighton, D. R. et al., "Role of Platelets and Fibrin in Healing Sequence," 196:4 *Annals of Surgery* 3790–388 (Oct. 1982).

Grotendorst, G.., "Can Collegen Metabolism be Controlled?" 24:9 *J. Trauma* S5–6, S49–54 (Sep. 1984) .

Grotendorst, G., et al. "Molecular Mediators of Tissue Repair," *Surgical Sci., Serv.* Ch. 2 p. 20–40 (1984).

Edited J. Linman; "Hemorrhagic Disorders"; Hematology, 849–894 (McMillan 1975).

Edited T. Hunt, et al.; "Role of Platelets in Wound Healing: Demonstration of Angiogenic Activity", Soft and Hard Tissue Repair, 380–394 (Praeger pre 1990).

Hemostasis and *Blood*Coagulation. (p. 99–111) (undated).

Grotendorst, G., et al. "Platelet–derived Growth Factor is a Chemoattractant for Vascular Smooth Muscle Cells," 113 *J. Cellular Phys.*, 261–266 (1982).

Knighton, D. et al., Classification and Treatment of Chronic Nonhealing Wounds, 204:3 *Annals of Surgery* 322–330 (Sep. 1986).

Curatech, Inc., Platelet Derived Wound Healing Formula (PDWHF), 1–14 (undated).

Ross, R. and Vogel, A., "The Platelet Derived Growth Factor," (undated.

(List continued on next page.)

*Primary Examiner*—David A. Reifsnyder
(74) *Attorney, Agent, or Firm*—Hahn Loeser & Parks LL; Laura G. Barrow

(57) ABSTRACT

A novel method for producing an autologous platelet rich blood composition is described. The resulting blood composition is useful in procedures for enhancing bone fusion, hemostasis, and repairing soft tissue in animals.

21 Claims, 2 Drawing Sheets

OTHER PUBLICATIONS

Zetter, B. and Antoniades, H., Stimulation of Human Vascular Endothelial Cell Growth by a Platelet–Derived Growth Factor and Thrombin, 11 *J. Supramolecular Structure* 361–370 (1979).

Banda, J., et al. "Isolation of a Nonmitogenic Angiogenesis Factor from Wound Fluid," 79 *Proc. Nat'l Acad. Sci. USA*, 7773–7777 (Dec. 1982).

"Polypeptide Transforming Growth Factors Isolated from Bovine Sources and Used for Wound Healing In Vivo," 219 *Science* 1329–1331 (Mar. 18, 1983).

Levi–Montalcini, "Repair Factor F.C.P." 1–41 (Oct. 1986).

Cope, L., Surgeon's Treatment Lets Patients heal Stubborn Wounds with Own *Blood*, from Mpls Star and Trib Nov. 12, 1984.

Grotendorst, G., et al. "Stimulation of Granulation Tissue Formation by PDGF in Normal and Diabetic Rats," *Laboratory of Dev. Biology and Anomalies NIH* (undated).

Time Magazine article of Oct. 7, 1985 on work done at Harvard Medical School.

Radioimmunoassay of human serum growth factor for Balb/c–3T3 cells; Derivation from Platelets by Antoniades et al. from vol. 74, Proc. Natl. Acad. Sci, U.S.A. (May 1977).

Robson, M., et al., "Platelet–Derived Growth Factor BB for the Treatment of Chronic Pressure Ulcers," 339 *The Lancet* 23–25 (Jan. 4, 1992).

Leitzel, K., et al. "Growth Factors and Wound Healing in the Hamster," 11:6 *J. Dermatol. Surg. Oncol.*, 617–622 (Jun. 1985).

Hunt, T., "Can Repair Processes by Stimulated by Modulators (Cell Growth, Angiogenic Factors, etc.) without Adversely Affecting Normal Processes ?" 24 *Frontiers in Understanding Burn Injury* S39–46 (Sep. 1984).

Senior, R., et al. "Chemotactic Activity of Platelet Alphia Granule Proteins for Fibroblasts, " 96 *J. Cell Bio.*, 382–385 (Feb. 1983).

Johnson, A., et al., "Platelet Derived Growth Factor: Identification of Constituent Polypeptide Chains," 104:1 *Biochem and Biophys. Res. Comm.*, 66–74 (Jan. 15, 1982).

Thornton, J. W., et al. "Epidermal Growth Factor in the Healing of Second Degree Burns: A Controlled Animal Study, " 8: *Burns* 156–160 (1981).

Greaves, M., "Lacke of Effect of Topically Applied Epidermal Growth Factor (EGF) on Epidermal Growth in Man In Vivo," 5: *Clin. And Exper. Derma.*, 101–103 (Aug. 1979)..

Devel, T., et al., "Platelet Factor 4 is Chemotactic for Neurtrophils and Monocytes, " 78:7 *Prac. Natl. Acad. Sci. USA*, 4584–4587 (Jul. 1981).

Niall, M., et al., "The Effect of Epidermal Growth Factor on Wound Healing in Mice," 83 *J. Surg. Res.* 164–169 (1982).

Carpenter, G., "The Regulation of Cell Proliferation: Advances in the Biology and Mechanism of Action of Epidermal Growth Factor," 71:5 *J. Invest. Derma.*, 283–288 (1978).

Frati, L., "Selective Binding of the Epidermal Growth Factor and its Specific Effects on the Epithelial Cells of the Cornea," 14 *Exp. Eye Res.* 134–141 (1972).

U.S. patent application Ser. No. 10/115,623, Brandt et al., filed Apr. 4, 2002.

* cited by examiner

METHOD FOR PRODUCING AUTOLOGOUS PLATELET-RICH PLASMA

BACKGROUND AND SUMMARY OF THE INVENTION

The present invention is directed to a method of processing blood to create an autologous platelet rich blood composition useful in the enhancement of bone fusion and soft tissue repair in animals.

DETAILED DESCRIPTION OF THE PREFERRED EMBODIMENTS

The present invention is directed to a novel method of processing blood to create a blood composition rich in platelets and fibrinogen for subsequent use in surgical enhancement of bone fusion and soft tissue repair. Specifically, the invention comprises, in certain aspects, combining platelet rich and platelet poor plasma components which have been centrifugually separated from whole blood drawn from a patient. These two components are combined in a preferred ratio, as discussed in more detail below, to create a composition useful in surgical bone growth enhancement, soft tissue repair procedures and as an aid in controlling surgical and traumatic hemostasis.

Figure 1:
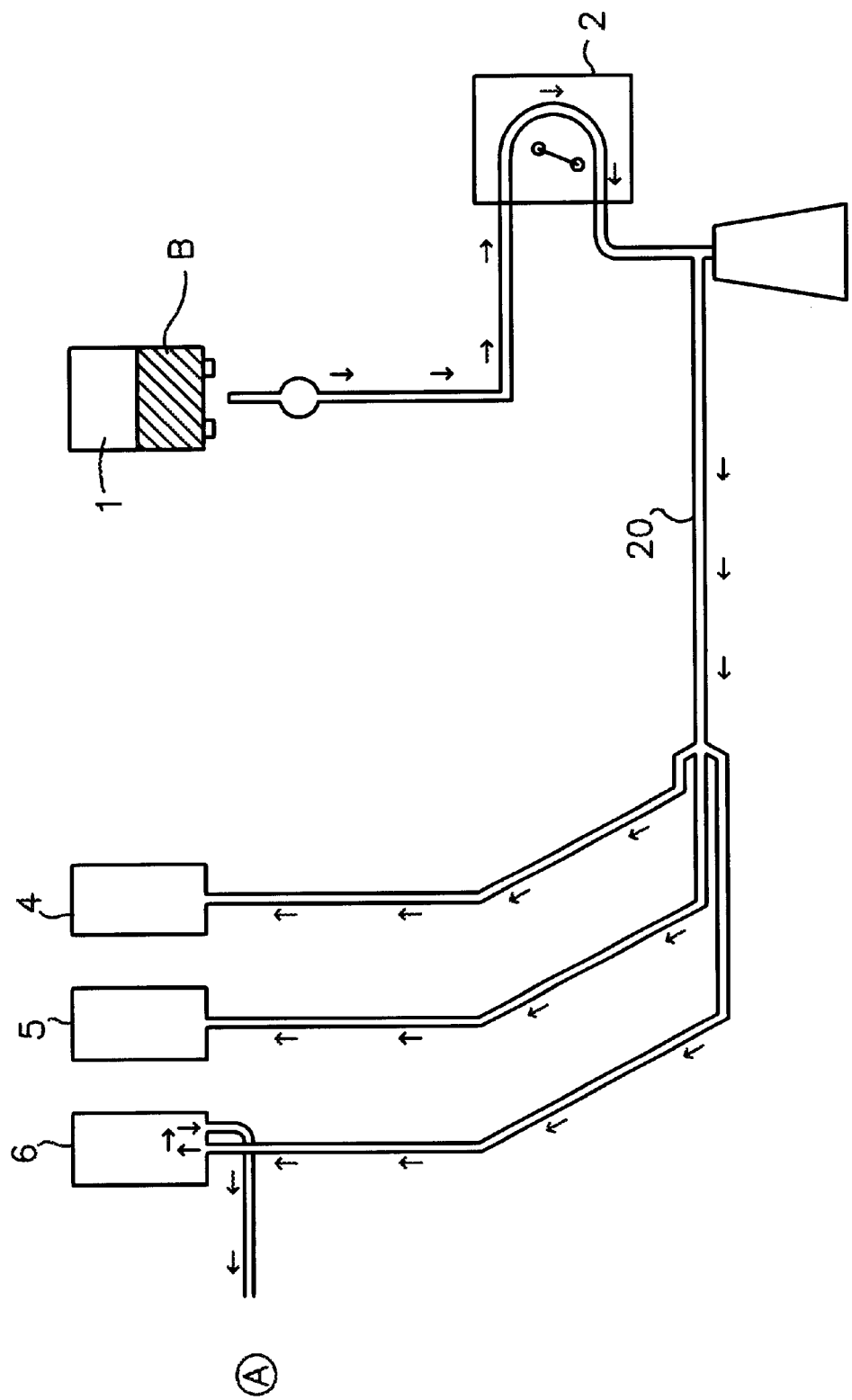
FIGS. 1 and 2 are schematics illustrating the overall process of the present invention.
Figure 2:
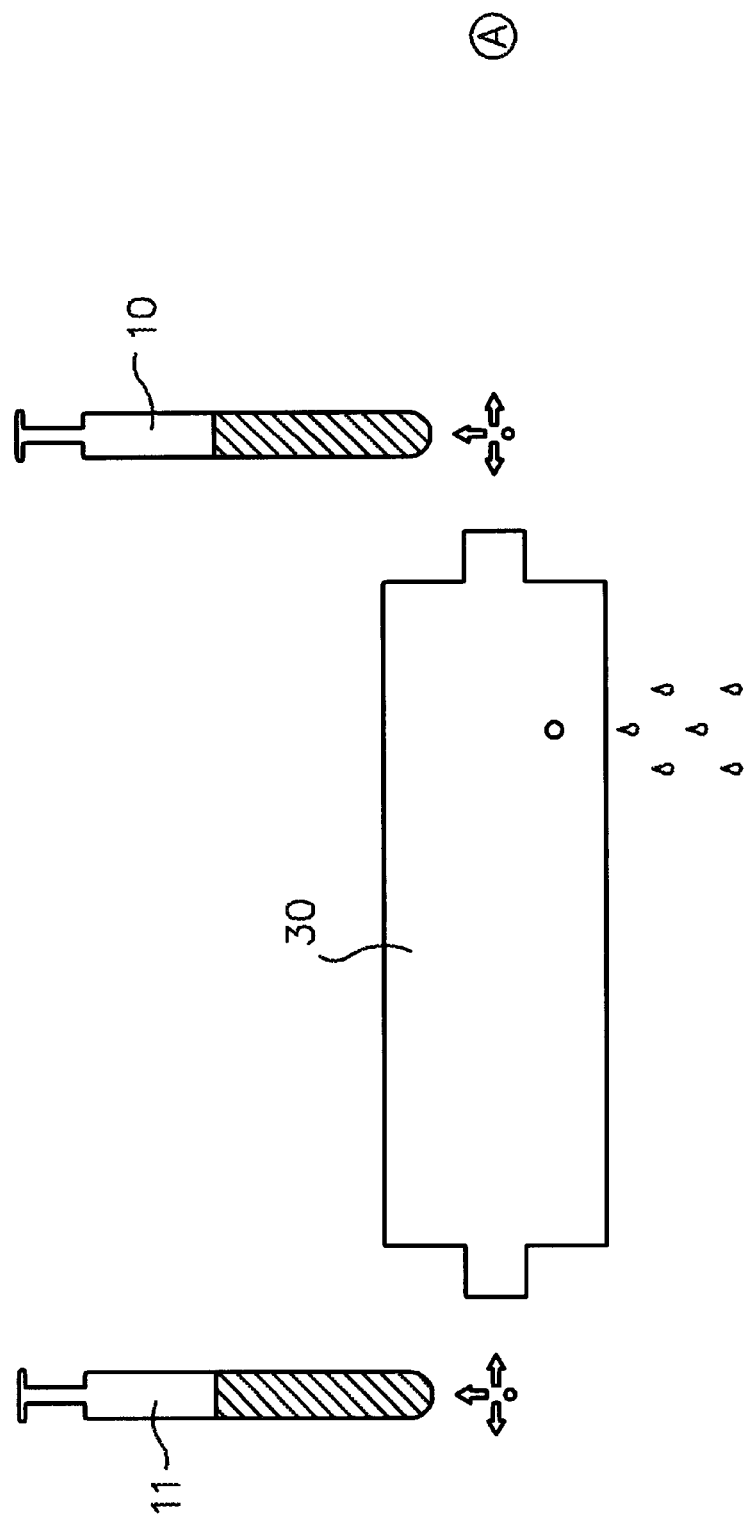

The inventive method first comprises obtaining about 200 to 500 milliliters of whole blood from a patient via conventional phlebotomization techniques. Preferably, the blood B is added to a collection container 1 (such as a conventional IV bag, for example) containing an anticoagulant, such as citrate phosphate dextrose adenine solution (CPDA), for example. As shown schematically in FIGS. 1–2, the blood is then channeled, via a pump 2, from the container 1 into a centrifuge bowl 3 which is spinning at about 5,000 to 6,000 RPM's, more preferably about 5,600 RPM's (i.e. a "hard" spin). During the centrifugation process, the blood is separated into three distinct components which, in turn, are eventually diverted into separated containers or bags 4–6. The first layer or component to be "spun off" is the "platelet poor plasma" component (hereinafter the "PPP component"), which is the lightest in density and composed primarily of plasma proteins. Preferably about 60 to 120 ml of the PPP component is removed from the bowl via a syringe 10 and set aside for further processing. The second separated layer is the buffy coat, which is largely composed of platelets and white blood cells, and finally the bottom layer is composed of packed red blood cells.

When the buffy coat is first detected during centrifugation, the centrifugal speed is reduced to about 2,000 to 3,000 RPM, more preferably about 2,400 RPM. At this point, the centrifuge is placed in "stand-by" mode for about 2 minutes, during which time the introduction of whole blood is stopped. This "soft" spin allows the maximum number of platelets remaining in the red blood cell layer to separate and migrate into the buffy coat layer, thereby producing a concentrated platelet rich plasma component (hereinafter the "PRP component").

The PRP component is then diverted into a separate container 5 as additional whole blood is manually introduced into the centrifuge every two to three seconds. The introduction of additional whole blood into the centrifuge bowl 3 serves to push the resulting PRP component out of the bowl and through the tubing 20 leading to the respective collection container 5 for the PRP component. This aspect of the process serves to "milk" out the platelet fraction through the buffy coat, thereby extracting the maximum amount of platelets from the patient's blood. This "milking" step is continued until about the first millimeter of packed red blood cells are entered, as evidenced by the detection of a "flame" entering the plasma already collected in the PRP collection container. For example, when a 55-ml centrifuge bowl is employed during the process, an additional 5 ml of blood is added after the "flame" is detected (for a 125 ml bowl, an additional 10 ml of blood is added upon detection of the "flame").

Once the PRP component has been removed, the remaining PPP component and red blood cells are diverted into a second collection bag 4 for holding and reprocessing. By reprocessing the remaining PPP/red blood cell components (i.e. centrifugal separation at 5,000 to 6,000 RPM's, followed by centrifugal separation between 2,400 to 3,000 RPM's, followed by the "milking" process as described above), the maximum amount of platelets may be removed. After the PPP/red blood cell component has been reprocessed a second time, the remaining red blood cells and PPP component are collected in the separate collection bag 4, for future re-infusion into a patient.

The PPP component originally extracted from the whole blood during the first centrifugal separation is processed through a hemoconcentrator 30, preferably a pediatric hemoconcentrator (shown schematically in FIG. 2), to which a negative pressure of up to 500 mm Hg has been applied (via a tumsent syringe or outside vacuum source), to extract out extracellular water, thereby reducing its volume by ⅚ while simultaneously increasing the fibrinogen levels normally found in the plasma. In the most preferred aspect of the present invention, only this PPP component is processed through the hemoconcentrator as opposed to the buffy coat. By not passing the buffy coat or PRP component through the hemoconcentrator, disruption of the platelet membranes is avoided, and the original concentration of platelets is maintained. Moreover, concentrating the original PPP component provides a more tenacious coagulum that is helpful in bonding together various bone fragments or bone fusion products, in providing a tighter matrix or scaffold for enticing the migration of osteoblasts and for the enhancement of hemostasis.

During the hemoconcentrating procedure, one syringe 10 is filled with a volume of PPP (preferably approximately 60 ml) while a second syringe 11 remains temporarily empty. The volume of PPP is manually pushed through the hemoconcentrator 30 and into syringe 10. Once the PPP volume from the first syringe 10 extracted, the direction of plasma flow is reversed and the PPP volume is pushed from syringe 11, back through the hemoconcentrator 30, and into syringe 10 again. As discussed above, this process of pushing the volume of PPP back and forth through the concentrator in the presence of a negative pressure of up to 500 mm Hg is continued until the volume of PPP fraction is reduced to about ⅚.

The resulting PRP and concentrated PPP components are then preferably combined in a ratio of 3 ml (PRP) to 1 ml (concentrated PPP) for optimal results; however, it will be recognized by the skilled artisan that blood compositions having different ratios of PRP to PPP may be employed, depending upon the intended therapeutic end use of the composition. This resulting composition may then be added to bone grafting material to aid in the enhancement of bone fusion (e.g. non-unionizing fractures of long bones, total joint replacement), soft tissue repair, oral surgery, and hemostasis, for example. The composition may even be sprayed or injected into various surgical areas or be forced by negative pressure, positive pressure, or a combination of both, into larger pieces of bone that will be used in the bone fusion process.

The final processed blood composition has a platelet count of between three to six times the native baseline count. For example, if a patient's platelet count is 250,000/µl, then the number of platelets in the inventive composition is within the therapeutic range of 1–1.5 mllon/µl.

For use of the final blood composition for bone grafting material, the bone or bone graft (not shown) is soaked in inactive blood composition for up to about sixty minutes prior to activation. The blood composition is activated by adding 1 ml of calcified thrombin solution (i.e. 5000 units bovine thrombin reconstituted with 10 ml or 1 gram of 10% calcium chloride) to every 10 ml of the inventive PRP/PPP composition.

The preferred equipment used to extract the whole blood into its separate components described herein may be any conventional centrifugation machine typically used in biomedical, and more specifically, blood processing, applications. An exemplary centrifuge is a DIDECO COMPACT ADVANCED, manufactured by Dideco (Italy). A preferred hemoconcentrator is the pediatric HEMOCOR brand hemoconcentrator, manufactured by Minntech (Minneapolis, Minn.).

The foregoing disclosure and description of the invention are illustrative and explanatory thereof, and various changes in the amounts and volumes of blood and blood components processed as well as equipment, may be made without departing from the spirit of the invention.

We claim:

1. A method for producing autologous platelet rich plasma, said method comprising:
   a. placing a volume of anticoagulated blood into a centrifuge machine and centrifugally separating said volume of blood, at a first speed, into a platelet poor plasma component, a buffy coat component, and a layer of red blood cells, said buffy coat component comprising platelets;
   b. transferring said platelet poor plasma component from said volume of blood to a first collection device;
   c. extracting additional platelets from said red blood cell layer into said buffy coat component to form a concentrated platelet rich plasma component;
   d. hemoconcentrating said platelet poor plasma component to produce a concentrated platelet poor plasma component; and
   e. combining said concentrated platelet poor plasma component with said concentrated platelet rich plasma component to form a platelet-rich composition.

2. The method of claim 1, wherein said concentrated platelet rich plasma component is combined with said concentrated platelet poor plasma component in a ratio of about 3:1.

3. The method of claim 1, wherein said first speed is at least 5,000 RPM and said extracting comprises reducing said first speed to a second speed of less than 5,000 RPM upon visual detection of said buffy coat component.

4. The method of claim 3, wherein said second speed is about 2,000 to 3,000 RPM.

5. The method of claim 4, wherein said second speed is 2,400 RPM.

6. The method of claim 3, wherein said concentrated platelet rich plasma component is combined with said concentrated platelet poor plasma component in a ratio of about 3:1.

7. The method of claim 5, wherein said concentrated platelet rich plasma component is combined with said concentrated platelet poor plasma component in a ratio of about 3:1.

8. A method for producing autologous platelet rich plasma, said method comprising:
   a. placing a volume of anticoagulated blood into a centrifuge machine and centrifugally separating said volume of blood, at a first speed, into a platelet poor plasma component, a buffy coat component, and a layer of red blood cells, said buffy coat component comprising platelets;
   b. transferring said platelet poor plasma component from said volume of blood to a first collection device;
   c. extracting additional platelets from said red blood cell layer into said buffy coat component to form a concentrated platelet rich plasma component;
   d. hemoconcentrating only said platelet poor plasma component to produce a concentrated platelet poor plasma component; and
   e. combining said concentrated platelet poor plasma component with said concentrated platelet rich plasma component to form a platelet-rich composition.

9. The method of claim 8, wherein said concentrated platelet rich plasma component is combined with said concentrated platelet poor plasma component in a ratio of about 3:1.

10. The method of claim 8, wherein said first speed is at least 5,000 RPM and said extracting comprises reducing said first speed to a second speed of less than 5,000 RPM upon visual detection of said buffy coat component.

11. The method of claim 10, wherein said second speed is about 2,000 to 3,000 RPM.

12. The method of claim 11, wherein said second speed is 2,400 RPM.

13. The method of claim 10, wherein said concentrated platelet rich plasma component is combined with said concentrated platelet poor plasma component in a ratio of about 3:1.

14. The method of claim 12, wherein said concentrated platelet rich plasma component is combined with said concentrated platelet poor plasma component in a ratio of about 3:1.

15. A method for producing autologous platelet rich plasma, said method comprising:
   a. adding a volume of anticoagulated blood into a centrifuge machine and centrifugally separating, at a first speed, said volume of blood into a platelet poor plasma component, a buffy coat component, and a layer of red blood cells, said buffy coat component comprising platelets;
   b. transferring said platelet poor plasma component from said volume of blood to a first collection device;
   c. upon visual detection of said buffy coat component, reducing said machine's centrifugation speed to a second speed;
   d. ceasing the addition of said whole blood into said centrifuge machine for a time sufficient to allow said platelets in said red blood cell layer to migrate into said buffy coat component to form a concentrated platelet-rich plasma component;
   e. resuming the addition of said whole blood into said centrifuge machine at least every 2 seconds, thereby further extracting said platelets from said red blood cell layer to form said concentrated platelet-rich plasma component;

f. hemoconcentrating said platelet poor plasma component to produce a concentrated platelet poor plasma component; and g. combining said concentrated platelet poor plasma component with said concentrated platelet rich plasma component to form a platelet-rich composition.

16. The method of claim 15, wherein said concentrated platelet rich plasma component is combined with said concentrated platelet poor plasma component in a ratio of about 3:1.

17. The method of claim 15, wherein said first speed is over 5,000 RPM and said extracting comprises reducing said first speed to a second speed of less than 5,000 RPM upon visual detection of said buffy coat component.

18. The method of claim 17, wherein said second speed is 2,000–3,000 RPM.

19. The method of claim 18, wherein said second speed is 2,400 RPM.

20. The method of claim 19, wherein said concentrated platelet rich plasma component is combined with said concentrated platelet poor plasma component in a ratio of about 3:1.

21. The method of claim 17, wherein said concentrated platelet rich plasma component is combined with said concentrated platelet poor plasma component in a ratio of about 3:1.

* * * * *